United States Patent
DeLegge

(10) Patent No.: US 7,291,160 B2
(45) Date of Patent: *Nov. 6, 2007

(54) INTRAGASTRIC CATHETER

(76) Inventor: Rebecca DeLegge, 3233 Cotton Field Dr., Mount Pleasant, SC (US) 29466

( * ) Notice: Subject to any disclaimer, the term of this patent is extended or adjusted under 35 U.S.C. 154(b) by 596 days.

This patent is subject to a terminal disclaimer.

(21) Appl. No.: 10/390,947

(22) Filed: Mar. 17, 2003

(65) Prior Publication Data

US 2004/0186503 A1 Sep. 23, 2004

(51) Int. Cl.
*A61M 29/00* (2006.01)

(52) U.S. Cl. .................................... 606/192; 604/909

(58) Field of Classification Search ........ 606/190–199; 604/103.07, 104, 99.04, 101.01, 909, 910, 604/916, 918, 907, 96.01, 99.01, 99.02, 103.08; 623/23.67, 23.65; 600/207
See application file for complete search history.

(56) References Cited

U.S. PATENT DOCUMENTS

| | | | | |
|---|---|---|---|---|
| 4,501,264 A * | 2/1985 | Rockey | .............. | 128/898 |
| 4,694,827 A * | 9/1987 | Weiner et al. | .............. | 606/192 |
| 4,739,758 A * | 4/1988 | Lai et al. | .............. | 606/1 |
| 4,878,495 A * | 11/1989 | Grayzel | .............. | 606/193 |
| 5,234,454 A * | 8/1993 | Bangs | .............. | 606/191 |
| 5,379,759 A * | 1/1995 | Sewell, Jr. | .............. | 600/207 |
| 5,868,141 A | 2/1999 | Ellias | | |
| 5,947,924 A * | 9/1999 | Liprie | .............. | 604/103.07 |
| 5,954,739 A * | 9/1999 | Bonutti | .............. | 606/190 |
| 6,013,054 A * | 1/2000 | Jiun Yan | .............. | 604/103.07 |
| 6,017,324 A * | 1/2000 | Tu et al. | .............. | 604/103.07 |
| 6,454,785 B2 | 9/2002 | Garza | | |
| 6,746,460 B2 * | 6/2004 | Gannoe et al. | .............. | 606/153 |
| 2005/0159769 A1 | 7/2005 | Alverdy | | |

FOREIGN PATENT DOCUMENTS

WO WO 02/071951 A1 9/2002

* cited by examiner

*Primary Examiner*—Anhtuan T. Nguyen
*Assistant Examiner*—Elizabeth Houston
(74) *Attorney, Agent, or Firm*—B. Craig Killough

(57) ABSTRACT

An intragastric catheter provides satiety due to its presence in the stomach cavity. Efficacy is improved by the tactile sensation provided by a plurality of fingers that extend from the device. Normal peristaltic action upon the device moves the fingers relative to the stomach. The structure of the intragastric catheter reduces the level of precision required in placement of the device, and blockage of conduits to and from the stomach by the device is unlikely.

5 Claims, 5 Drawing Sheets

INTRAGASTRIC CATHETER

FIELD OF THE INVENTION

This invention relates to medical devices generally, and is more specifically related to an intragastric catheter that is useful in the treatment of obesity.

BACKGROUND OF THE INVENTION

Morbid obesity is a major medical problem affecting millions of people. Many serious health problems are associated with morbid obesity, including hypertension, hyperlipidemia, exacerbation of diabetes mellitus, heart disease, degenerative arthritis, and Pickwickian syndrome, certain types of cancer, gallstones, varicose veins, thromboembolism and hernias. Additionally, morbid obesity can lead to psychosocial difficulties such as depression, loss of self-esteem and decreased employability.

Attempts to induce weight loss in morbidly obese patients have been largely unsuccessful. Diet, exercise and behavioral modification are usually not effective in the long term because the morbidly obese patient does not maintain adherence to these programs. Further, such programs may risk further damage to the patient's health. The long term use of pharmaceuticals in bariatric medicine is also problematic. Use of pharmaceutical agents may lead to addiction, undesired side effects, and/or loss of potency due to drug tolerance.

Surgical procedures that have been applied include jejunoileal or gastric bypass surgery, gastroplasty and gastric stapling and oral surgical procedures such as wiring shut the patient's jaws to reduce food intake. These procedures are effective in producing weight loss, but are invasive, with associated risks and recovery times, as well as being expensive and often ineffective over the long term.

Various intragastric inflatable balloon devices have been heretofore used. These devices occupy the stomach cavity, thereby reducing its volume, and providing satiety. Problems associated with these devices include undesired deflation, requiring surgical removal, and ulceration or necrosis created by constant pressure of the device on the stomach wall and gastric outlet obstruction.

Placement of devices by a percutaneous endoscopic gastrostomy (PEG) procedures, while less expensive than surgical procedures, are less precise. Balloon type intragastric catheters positioned by PEG procedures, as described in De Hoyos Garza, U.S. Pat. No. 6,454,785, may block only a portion of the stomach, or they may block entry to the stomach from the esophagus if the device is not precisely positioned.

SUMMARY OF THE PRESENT INVENTION

An intragastric catheter provides satiety due to its presence in the stomach cavity. Efficacy is improved by the tactile stimulation provided by a plurality of fingers that extend from the device. Normal peristaltic action upon the device moves the fingers relative to the stomach. The structure of the intragastric catheter reduces the level of precision required in placement of the device, and blockage of conduits to and from the stomach by the device is reduced.

DESCRIPTION OF THE PREFERRED EMBODIMENTS

Figure 1:
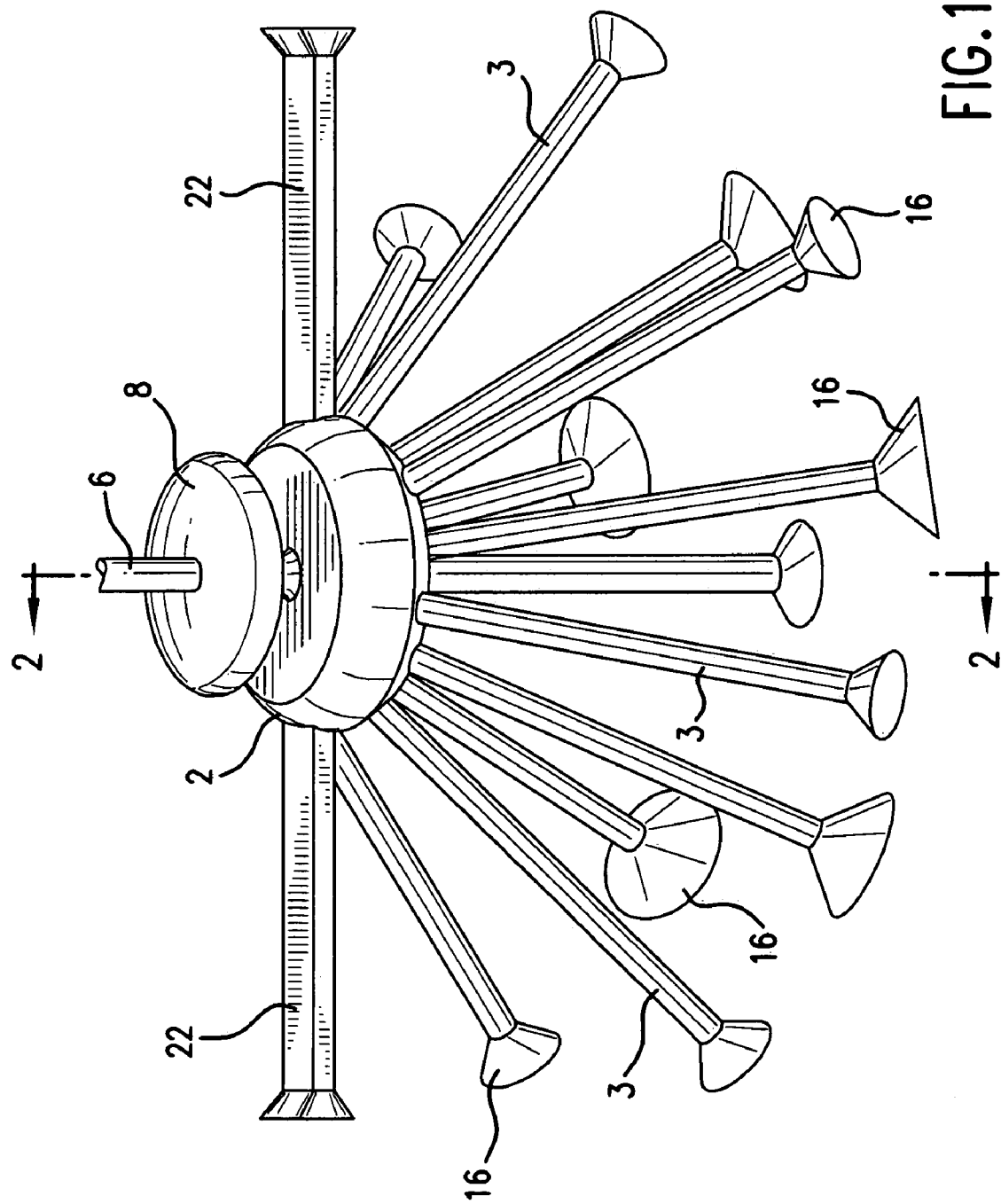
FIG. 1 is a perspective view of the intragastric catheter.
Figure 2:
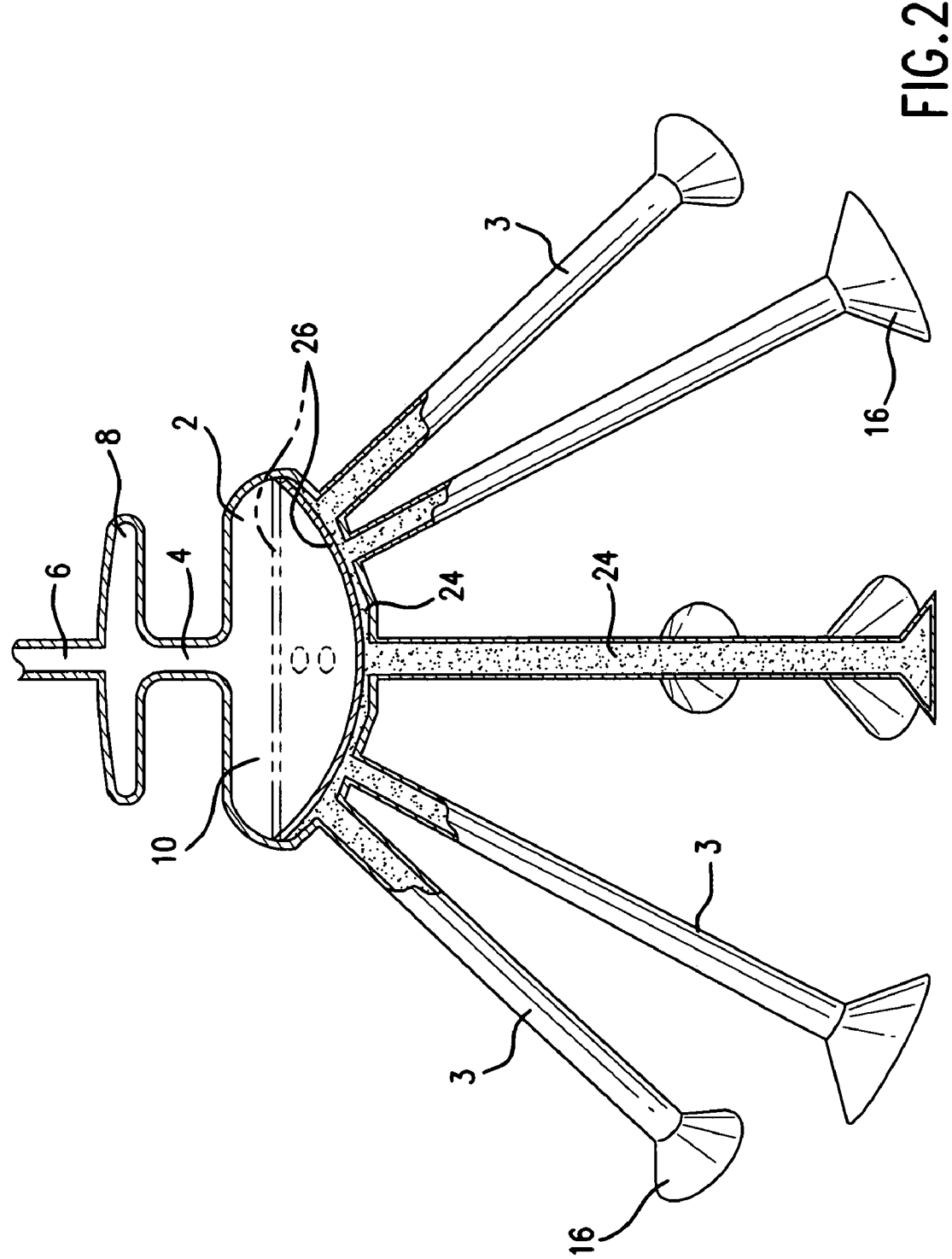
FIG. 2 is a sectioned view of the intragastric catheter, taken essentially along line 2-2 of FIG. 1.

Referring now to FIG. 1, the intragastric catheter comprises a bladder 2. A plurality of finger-like tubules 3 extend from various locations on the lower surface of the bladder. In the embodiment as shown, a neck 4 connects a bolster to the bladder, and an external tube 6 extends from the internal bolster 8. External bolster 9 assists in holding the device in place within the stomach.

In the preferred embodiment, the bladder contains a fluid 10. The fluid may be a gas, a liquid, or a gel, or a mixture thereof, or a combination thereof. The fluid is provided to the bladder through external tube 6. A valve 28 may be present that communicates with the bladder. Increasing or decreasing the volume and pressure of fluid that is present in the chamber variably inflates the bladder.

In the preferred embodiment, the finger-like tubules are hollow, with the hollow space in the tubules communicating with the bladder to provide for a transfer of fluid. Accordingly, as the bladder is filled with fluid, the fluid flows into tubules, providing additional rigidity for the tubules, according to the volume and pressure of the fluid that is present in the chamber. The chamber acts as a reservoir to supply fluid to the tubules.

Figure 3:
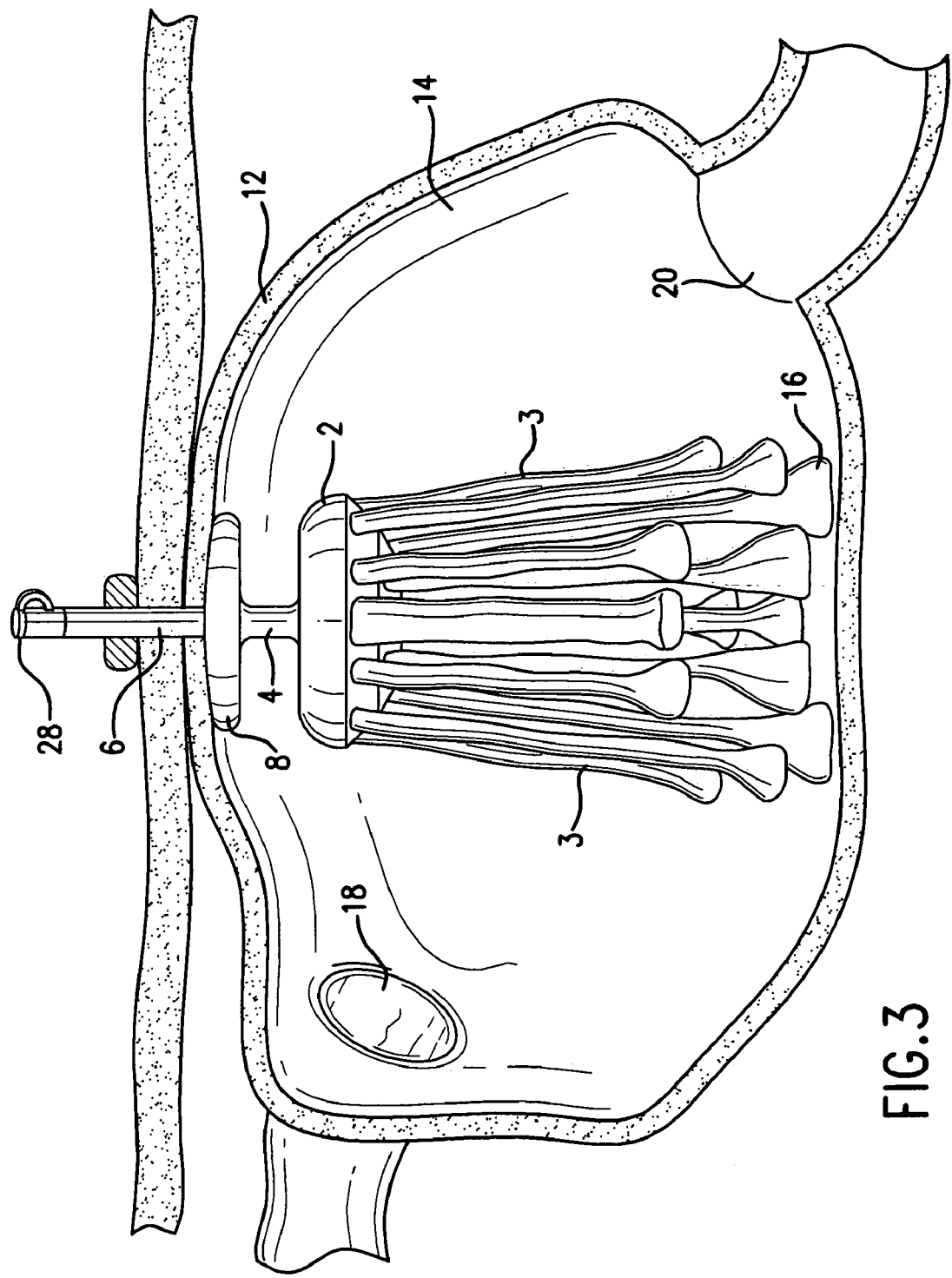
FIG. 3 is a side elevation of an intragastric catheter in the deflated state and positioned within a user's stomach.

The tubules are flexible, and are capable of a deformation relative to the bladder. Particularly at the point of attachment of the tubules to the bladder, the tubules may be displaced relative to the bladder. As normal peristaltic action of the stomach 14 causes the device to be moved about within the stomach, the ends of the tubules that are opposite the bladder are dynamic. Movement of the tubules from peristaltic action provides a tactile sensation against the wall of the stomach, which provides satiety. The tubules may be variably inflated by the device as required, to provide the desired tactile stimulation. If the tubules are substantially deflated, so that they are flaccid, as shown in FIG. 3, then little tactile stimulation will occur. On the other hand, over inflation may result in insufficient movement of the tubules. Movement of the tubules due to peristaltic action prevents the tubules from constantly contacting a single point of the stomach wall, thereby reducing necrosis or ulceration due to constant contact of the tubules with the stomach wall. In the preferred embodiment, the tubules have an enlarged end 16 that increases tactile stimulation. In the particular embodiment shown in the drawing figures, the enlarged end has a recess that is centrally disposed within the end. This recess in the end of the tubules helps reduce constant contact of the end of the tubules with the stomach wall by reducing the amount of surface area that comes in contact with the stomach wall.

Figure 5:
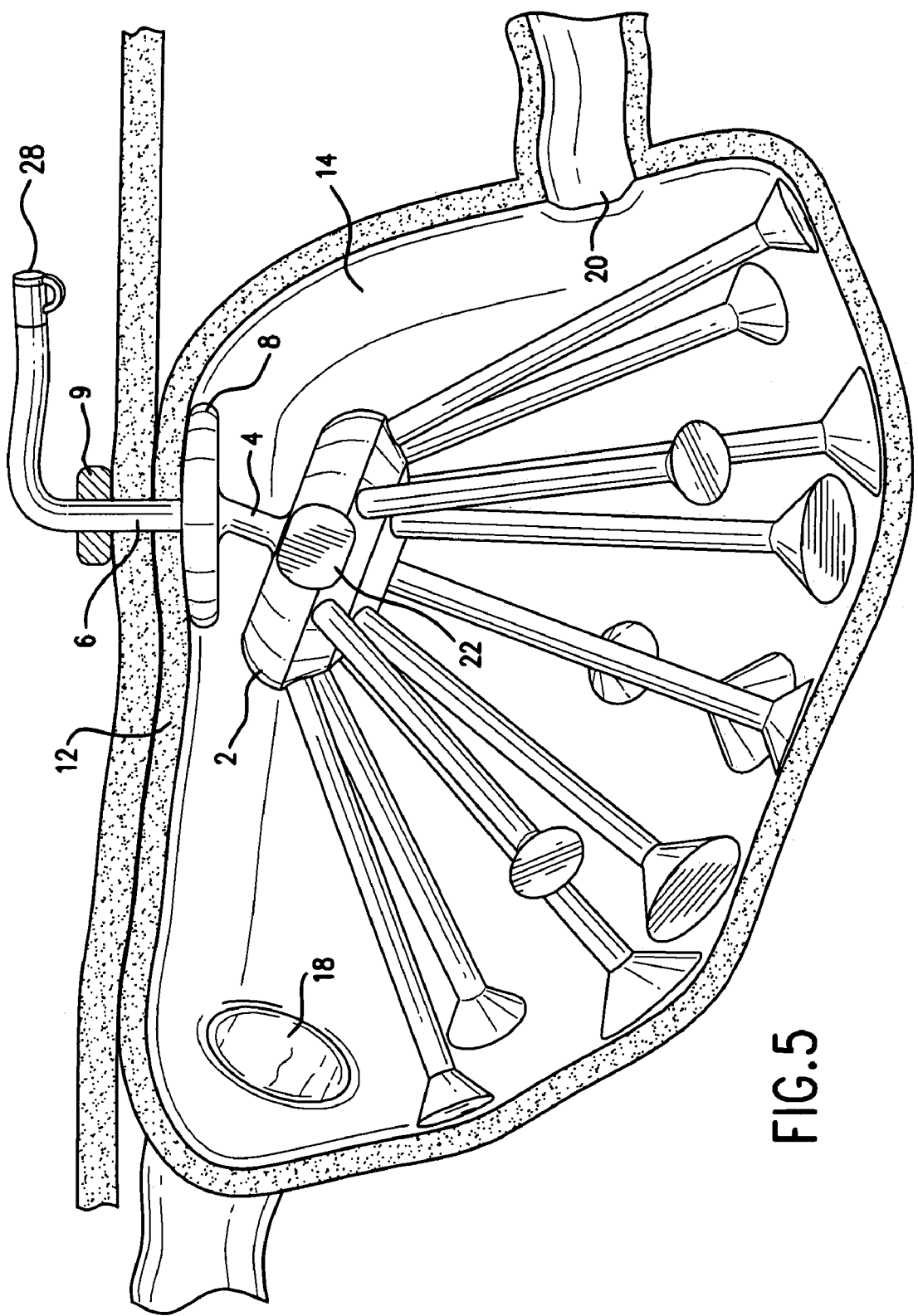
FIG. 5 is a side elevation of an intragastric catheter in the inflated state and positioned within a user's stomach.

The neck 4 of the device is deformable, which insures proper orientation of the device relative to the stomach. FIG. 5. The bolster 8 is adjacent to the stomach wall 12, while the neck allows the remainder of the device to bend relative to the bolster. Accordingly, if the device is positioned by a PEG procedure, and placement of the device is not optimal, the device deforms relative to bolster by means of the neck, so that the tubules contact the stomach wall. For example, if the placement is too high relative to optimal placement, the neck bends to allow the device to enter the relatively lower part of the stomach. The use of the finger like tubules, rather than a massive object like a balloon, prevents blockage of the entry 18 or exits 20 of the stomach.

Longer tubules 22 may be used to orient the device upon placement. As shown, tubules 22 from a higher point of the bladder when the device is positioned as in FIG. 1. Tubules 22 extend from the bladder and opposite each other, and are generally horizontally when inflated and when the device is positioned as shown in FIG. 1. These longer tubules help position the device. They are positioned by peristalsis and/or at placement so as to find the long axis of the stomach. If they are placed on the short axis, the stomach will move them to the position of least resistance.

In one embodiment of the invention, a valve is present where the tubule joins the bladder. The valve allows the tubule to be filled with fluid, but prevents fluid from returning to the chamber. In case of a leak in a particular tubule, the fluid will leak into the stomach from that tubule and it will become deflated. However, it is not necessary to replace the entire catheter as a result of the deflation of one, or a few, of the tubules, since the remainder of the device will remain inflated. The valves could be positioned within the tubules, near the end of the tubule that joins the bladder, or the valves could be positioned within the bladder near the entrance to the tubules.

In one embodiment of the bladder, a diaphragm 22 is present within the bladder. A fluid 24, which is preferred to be a liquid, a gel, or a mixture thereof, is present on one side of the diaphragm. This side of the diaphragm communicates with the tubules. A fluid 10 under pressure, which could be air, is present on the other side of the diaphragm, and is provided through the external tube. As the fluid pressure in the bladder is increased, the liquid pressure on the opposite side the diaphragm is increased, and the pressure and volume within the tubules is increased. While the use of the liquid or a gel to fill the tubules is preferred, handling and pressurizing a liquid or gel is more difficult for the patient, than is the application of air pressure. The patient may easily apply pressure to the device using an air pump, whereas attempting to pressurize a liquid or gel by the insertion of additional liquid or gel material under pressure is more difficult.

The device may be constructed of suitable materials that will inflate or deflate when filled with a fluid. In a preferred embodiment, the device could be constructed of medical grade polyethylene terephthalate (PET). PET allows the device to have deformation characteristics similar to plastic storage bags that are commonly used in the kitchen, making it a suitable candidate for replacement by means of a percutaneous endoscopic gastrostomy (PEG) procedure as described herein. The tubules may be formed of two or more plies of material. For example, a 2-ply tubule will have better resistant to breakage or puncture than will a single ply tubule.

The intragastric catheter of the present invention may be introduced through the mouth, subsequently traveling through the esophagus and into the stomach. The abdominal wall is punctured, and a guide wire is inserted from the outside into the fundus of the stomach. The endoscope is grasped with the guide wire, and one end of the guide wire is extracted by pulling the endoscope out of the mouth while the other end of the guide wire remains outside of the abdomen. The intragastric catheter is placed through the abdominal wall by attaching the intragastric catheter to the guide wire extended out of the patient's mouth and pulling on the other end of the guide wire until the intragastric catheter is pulled through the puncture opening in the abdominal wall. The placed intragastric catheter is secured on the stomach wall with the bolster.

Figure 4:
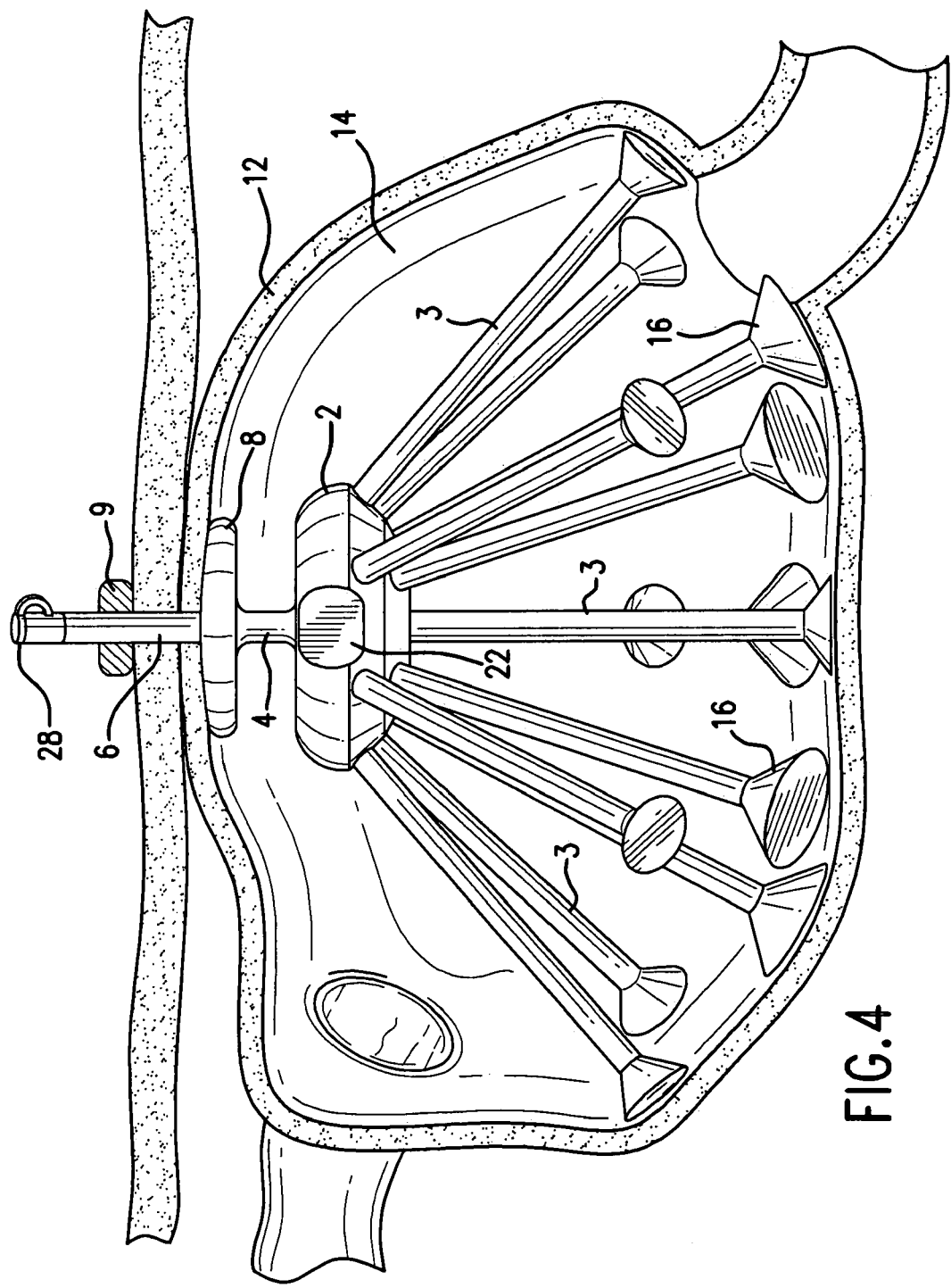
FIG. 4 is a side elevation of an intragastric catheter in the inflated state and positioned within a user's stomach.

FIGS. 3 through 5 show the intragastric catheter as it is positioned intragastrically within the obese person. The intragastric catheter has multiple finger like tubules that are subject to the peristalsis within the stomach, which causes movement of the tubules to prevent pressure from being constantly applied on one surface of the stomach, and thereby preventing gastric erosion. The tactile sensation provided by the finger like tubules against the stomach provides satiety, and suppresses the patient's appetite.

What is claimed is:

1. A percutaneous intragastric catheter, comprising:
   a) a bolster for positioning the percutaneous intragastric catheter against an interior wall of a stomach;
   b) a tube for extension through a stomach wall and into said stomach, said tube comprising a neck that extends from said bolster wherein said neck is flexible for flexing within said stomach and relative to said stomach wall by peristaltic action;
   c) a bladder that communicates with said neck, wherein said bladder is spaced apart from said bolster by said neck, and said bladder is adapted to move within said stomach by flexing of said neck; and
   d) a plurality of elongated flexible tubules extending from said bladder that are flexible relative to said bladder and are flexed relative to said bladder by peristaltic action within said stomach.

2. A percutaneous intragastric catheter, as described in claim 1, wherein said bladder and said tubules are inflatable and deflatable in situ through said neck.

3. A percutaneous intragastric catheter, as described in claim 2, wherein said intragastric catheter further comprises a valve that communicates with said neck and said bladder.

4. A percutaneous intragastric catheter as described in claim 2, wherein said bladder has a fluid therein, and wherein each of said plurality of tubules communicates with said bladder and said plurality of tubules are formed to receive a portion of said fluid from said bladder.

5. A percutaneous intragastric catheter as described in claim 1, wherein each of said plurality of tubules has an enlarged end that is opposite an end of each of said plurality of tubules that is adjacent to said bladder.

* * * * *